United States Patent [19]
Wall

[11] 3,951,136
[45] Apr. 20, 1976

[54] MULTIPLE PURPOSE ESOPHAGEAL PROBE

[75] Inventor: Terence D. Wall, Ridgewood, N.J.

[73] Assignee: Vital Signs, Inc., Ridgewood, N.J.

[22] Filed: Oct. 7, 1974

[21] Appl. No.: 512,875

Related U.S. Application Data

[63] Continuation-in-part of Ser. No. 404,896, Oct. 10, 1973, abandoned.

[52] U.S. Cl. .......................... 128/2.06 E; 128/2 H; 128/2.05 S; 128/404; 128/DIG. 4
[51] Int. Cl.² .......................................... A61B 5/02
[58] Field of Search .................. 128/2.06 E, 2.06 R, 128/2 R, 2.05 R, 2 H, 2 K, 2.05 S, 351, 404, 418, 419 P, DIG. 4; 181/137

[56] References Cited
UNITED STATES PATENTS

| | | | |
|---|---|---|---|
| 3,081,765 | 3/1963 | Kompelien | 128/2 H |
| 3,480,003 | 11/1969 | Crites | 128/2.1 E |
| 3,499,435 | 3/1970 | Rockwell et al. | 128/2.06 E |
| 3,530,850 | 9/1970 | Edwards | 128/2.05 S |
| 3,533,403 | 10/1970 | Woodson | 128/2.06 E |
| 3,581,570 | 6/1971 | Wortz | 128/2 H |
| 3,734,094 | 5/1973 | Calinog | 128/2.06 E |

FOREIGN PATENTS OR APPLICATIONS

| | | | |
|---|---|---|---|
| 2,003,138 | 7/1971 | Germany | 128/2.06 E |
| 233,160 | 5/1969 | U.S.S.R. | 128/2 H |
| 229,727 | 10/1969 | U.S.S.R. | 128/2.1 E |

OTHER PUBLICATIONS

Ganz et al., "Newer Applications . . . Disease," J. Assn. of Adv. Med. Inst., Vol. 6, No. 2, Mar./Apr. 1972, p. 167.

Sikorski et al., "Malfunction Esoph . . . Research," J. Assn. Adv. Med. Inst., Vol. 6, No. 2, Mar./Apr. 1972, pp. 190–191.

Kavan et al., "Esophageal ECG Electrode," Anesthesis & Analgesic, Vol. 44, No. 1, Jan.–Feb. 1965, pp. 20–24.

*Primary Examiner*—Robert W. Michell
*Assistant Examiner*—Lee S. Cohen
*Attorney, Agent, or Firm*—Lowe, King, Price & Markva

[57] ABSTRACT

A single esophageal probe incorporating multiple different function components whereby a single multipurpose device is provided. A temperature sensor projects through and beyond the open inner end of the probe for substantially complete exposure, enclosed only by a thin protective membrane which also encloses a plurality of sound passing openings in the inner portion of the probe tube. In addition, pair of smooth tube mounted electrodes are provided for both electrocardiogram and emergency pacing purposes. The outer end of the tube mounts a connector block including plugs for engagement with the various interpretative instruments.

9 Claims, 5 Drawing Figures

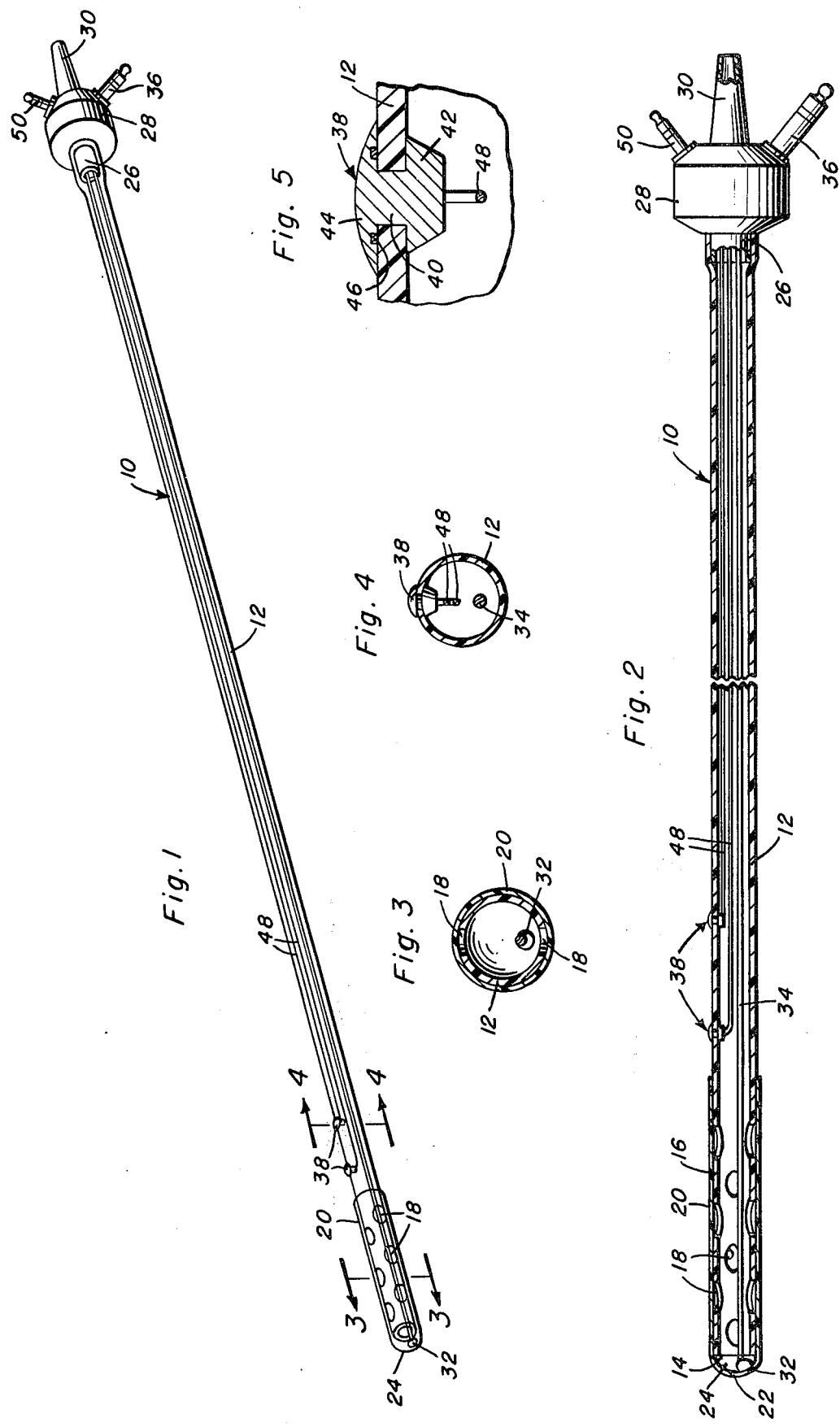

MULTIPLE PURPOSE ESOPHAGEAL PROBE

RELATION TO COPENDING APPLICATION

The present invention is a continuation-in-part of my U.S. Pat. Application, Ser. No. 404,896, filed Oct. 10, 1973, entitled "Multiple Purpose Esophageal Probe", now abandoned.

BACKGROUND OF THE INVENTION

The present invention generally relates to esophageal probes, and is more particularly concerned with a multi-purpose probe constructed so as to enable the use of a single probe in performing a plurality of functions in addition to the basic monitoring of heart and lung sounds simultaneously therewith and utilizing a probe which, insofar as the introduction and removal thereof relies on standard procedures.

Present medical technology permits medical personnel to monitor core body temperature, heart and lung sounds, electrocardiogram, and to pace the heart. However, these procedures are normally accomplished by four separate independent devices.

For example, heart and lung sounds may be monitored by a conventional stethoscope connected to a chest piece or an esophageal catheter. The esophageal catheter or probe is preferred because of the superior quality of the heart and lung sounds picked up in the esophagus versus the external chest wall.

Core body temperature, under present procedures, can be monitored by means of an esophageal temperature probe connected to an electronic temperature display. However, the conventional esophageal temperature probes are difficult to pass down the esophagus due to their small diameter and may not in fact reach the proper position in the lower one-quarter of the esophagus. Further, the temperature probe may be easily displaced during intubation, extubation, or manipulation of paraesophageal structures as a result of their small diameter. Also, the prior art esophageal temperature probes either were exposed to gastric juices in the esophagus, resulting in adverse biological effects to the patient and possible deterioration of electric connections between the probe and leads connected to it, or had a poor response time because of being inside of a tube having a long thermal time constant.

The conventional electrocardiogram or ECG is obtained by electrodes placed on the patient's chest or limbs. However, this is difficult to do in many surgical procedures such as thoracic and open heart surgery, burn cases and spinal operations.

BRIEF DESCRIPTION OF THE INVENTION

The invention herein contemplates the performance of all of these procedures utilizing a single multi-purpose esophageal probe similar in size and basic manner of manipulation to a heart and lung sound monitoring probe.

The probe of this invention includes an elongated plastic, preferably polyvinylchloride, tube having an open inner end with the inner portion of the tube provided with a plurality of sound passing openings therethrough. The openings as well as the open inner end of the tube are enclosed by a thin protective or diaphragm which excludes various body fluids while providing substantially no inhibition to the transmission of sound. The second or outer end of the tube mounts an enlarged rigid plastic block including a stethoscope mounting stem including a bore therethrough which extends through the block into direct communication with the interior of the tube for the desired heart and lung sound pickup.

The diaphragm over the open end of the tube bulges or extends slightly therefrom and internally accommodates a core temperature sensing element slightly beyond the open end of the tube and surrounded only by the extremely thin diaphragm whereby an exact reading can be obtained. The conductor extending from the temperature sensing element extends internally through the more rigid probe tube whereby the basic external size of the probe is not increased and the greater stability of the tube insures a proper positioning of the temperature sensing element as well as a retention of the element against accidental displacement and an assurance that the element will be positioned where desired, preferably within the lower one-quarter of the esophagus.

Provision for an ECG is effected by incorporating a pair of smooth non-irritating active electrodes mounted in the lower end of the tube to monitor electrocardiogram signals generated at spaced points in the esophagus. The active electrodes are connected to positive and negative input terminals of a differential amplifier of a standard ECG monitoring equipment. The amplifier includes ground input and output terminals; typically in the prior art the ground input terminal of the amplifier is connected to an electrode secured on the external part of the patient's body. The ground connection is necessary because in typical prior art ECG monitors the voltage derived from the active electrodes is so low that it cannot easily be amplified without unacceptable noise being introduced. By utilizing a pair of active electrodes in the esophagus, it has been found that a large enough electrocardiogram signal is derived to obviate the need for any further ECG electrode and in particular there is no connection from the patient to the amplifier input ground terminal.

By eliminating the ECG ground connection to the patient, there is provided a considerable safety advantage over the prior art. In particular, current from any electronic equipment being used on the patient, e.g., electrocathetering devices and other monitoring equipment, seeks a ground path if the equipment is not properly connected. Improper connections of these equipments occasionally occur because of various reasons, such as patient movement and broken leads, and can result in burning of the patient at a ground location other than that provided for the equipment. Also, damage to the heart of the patient in response to current coupled to an ECG ground electroode can result if there are problems with other electronic equipments connected to the patient. It has been found that the incorporation of the electrodes in the esophageal probe provides a much larger signal to noise ratio because of the proximity of the esophagus to the heart. An esophageal ECG is similar in pattern to an intra-cardiac ECG. The "P" waves look much like miniature QRS waves. This enhances the diagnosis of atrial and ventricular arrythmias and conduction defects. Further, the esophageal probe ECG makes the monitoring of the ECG easier by reducing artifacts on the ECG caused by patient movement or movement of the electrodes or dead wires, or poor electrical conduction between the electrode and the skin, and at the same time substantially reduces the time involved as compared to the necessity of attaching three or four electrodes and lead wires to the monitor.

Other objects and advantages of the invention which will subsequently become apparent reside in the details of the construction and manner of use as more fully hereinafter set forth, reference being had to the accompanying drawings wherein like numerals refer to like parts throughout.

BRIEF DESCRIPTION OF THE DRAWING

FIG. 1 is a perspective view of the multi-purpose esophageal probe of the invention;

FIG. 2 is a longitudinal cross-sectional view through the multi-purpose probe;

FIG. 3 is an enlarged cross-sectional detail taken substantially on a plane passing along line 3—3 in FIG. 1;

FIG. 4 is an enlarged cross-sectional detail taken substantially on a plane passing along line 4—4 in FIG. 1; and FIG. 5 is an enlarged sectional detail illustrating one of the mounted electrodes.

DETAILED DESCRIPTION OF THE INVENTION

Referring now more specifically to the drawing, reference numeral 10 is used to generally designate the multi-purpose esophageal probe comprising the instant invention. This probe includes an elongated, relatively rigid polyvinylchloride tube 12 of a diameter and length generally conforming to a heart and lung sound transmitting esophageal stethoscope and that is adapted to be inserted into the esophagus from an external body cavity, e.g., the mouth or nose.

The lower end of tube 12, adapted to be inserted into the lower portion of the esophagus, has a completely open inner or leading end 14, such constituting the end inserted into the body of a patient. The leading end portion 16 of the tube 12, for approximately 2 inches rearward of the leading or inner end 14, is provided with a series of openings or holes 18 therethrough to enable the substantially unencumbered transmission of heart and lung sounds to the interior of the tube 12. These holes 18, as well as the open leading end 14 of the tube 12 are enclosed by an extremely thin, latex membrane-like cuff or diaphragm 20 received thereover in the manner of a sleeve and affixed by thermoplastic bonding to the tube just rearward of the openings 18. This diaphragm 20 includes a forwardly extending bulbous tip portion 22 which forms a small chamber 24 forward of the leading end 14. This diaphragm 20 is specifically provided so as to exclude gastric juices from the tube 12 with the extremely thin nature of the membrane or diaphragm having substantially no effect on the sound transmission accommodated by the holes 18. It is thus seen that the lower end of the tube includes a thick, rigid wall segment and a thin wall segment. The thin wall segment is formed by the thin diaphragm 20 and openings 18, in combination with the opening at the tip, while the unperforated remainder of the lower end forms the thick tube segment. The thin wall segment has a low acoustic impedance relative to the thick wall segment. Thereby, the thin wall segment couples acoustic heart sounds to the interior of tube 12 and to a stethoscope or acoustic monitoring equipment that is connected to the end of the tube extending out of the body cavity.

The second end of the tube 12 is frictionally received over a hollow cylindrical projection 26 on a plastic connector or connector block 28. The connector 28 also includes, opposed from the projection 26, an elongated tapered stem 30 with which a standard stethoscope can be frictionally engaged. The full length taper of the stem 30 is of significance in insuring a proper tight frictional engagement between the stem and a stethoscope, as well as the accommodation of slight variations in the size of the connecting portion of the stethoscope. This stem 30 is also of course hollow with there being a sound transmitting passage through the stem 30, the mounting projection 26 and intermediate portion of the connector 28.

Another function of the multi-purpose esophageal probe 10 is to monitor core body temperature. As such, an appropriate temperature-electric transducer, such as a thermistor or thermocouple 32, is provided immediately foward of the portion of the thin wall segment formed at the tip or open, leading end 14 of the tube 12 within the diaphragm defined chamber 24. Exposed in this manner, aside from the extremely thin protective membrane at the diaphragm tip 22, very good response time is achieved because the thin wall segment has a very fast thermal time constant. In other words, due to the close proximity of the sensing element 32 to the thin membrane 20, and the fact that only this membrane 20 separates the element 32 from complete, virtually hemispherical exposure within the body, any temperature changes will be sensed immediately, contrary to the situation which would arise were the sensing element 32 at some internal point within the tube 12. Thus, the desired sensitivity is achieved in conjunction with the provision of means for positively inserting and positioning the temperature sensing element 32 as desired. In actual use, it has been found that for a 0.5° C temperature change there is a twenty minute difference in the response time of temperature sensor 32 when it is located immediately in proximity to the thin wall segment at the tip of tube 12 at leading end 14 relative to the sensor being adjacent the thick wall segment, about 1 inch from the tip and away from any of openings 18. This is the same time spread as exists between rectal temperature sensors and prior art esophageal temperature transducers wherein the transducer is exposed to gastric juices in the esophagus. While temperature transducer 32 is preferably located at the tip of tube 12, it is to be understood that other positions of the temperature transducer adjacent other thin wall segments of the tube are feasible. Generally, the temperature transducer would be located on the portion of tube 12 which is normally situated in the lower mediastinum, below the pulmonary veins, and between the heart and the descending portion of the aorta, a distance typically about 45 centimeters from the nostril.

The temperature sensing element or thermistor 32 is soldered to a piece of two-conductor shielded cable 34 with soldered connections of the thermistor covered and insulated by an appropriate medical adhesive. The shielded cable 34 extends completely through the interior of the tube 12 and internally into the connector or connector block 28 where it is connected to an outwardly extending miniature phone plug 36 also appropriately sealed to the connector 28. The plug 36 provides a convenient means of connection to an appropriate temperature monitoring device externally of the body. It will be noted that the plug 36 angles away from the stethoscope stem 30 for a simultaneous non-interfering use of both.

The multi-purpose probe 10 also includes electrocardiogram monitoring capabilities. In connection therewith, a pair of active silver plated brass or other suitable material electrodes 38 are mounted on the rigid, thick wall segment of the tube 12 immediately above the diaphragm 20 with the electrodes 38 being spaced approximately 1 ⅜ inches from each other. Electrodes 38 are referred to as active electrodes because they are connected to positive and negative input terminals of an ECG differential amplifier having ground input and output terminals that are not connected to the patient. With reference to FIG. 5 in particular, it will be noted that each electrode 38 includes a stem-like central portion 40 received through an aperture in the tube 12 and enlarged inner and outer heads 42 and 44 fixing the position of the electrode 38. The outer head 44 is provided with an annular adhesive receiving groove 46 in the tube engaging undersurface thereof which accommodates an appropriate medical grade adhesive for both securing and sealing the electrode 38 to the tube 12 whereby entry of gastric juices and the like is precluded. Also of significance with regard to each electrode 38 is the configuration of the outer head 44, such being of a low dome-like shape with peripheral edges tapering smoothly to the surface of the tube so as to avoid any scraping or irritation of the esophagus. It is to be understood that other electrode configurations can be employed, e.g., longitudinally spaced bands can be wrapped around the thick wall segment, as long as the electrodes are smooth and are formed of a highly conductive material to provide a high signal to noise ratio.

Both electrodes 38 are appropriately soldered to lengths of insulated wire 48 which extend internally through the tube 12 and into the connector 28 where they are in turn soldered to an appropriate subminiature phone plug 50 distinctly angled away from both the substantially larger temperature monitoring plug 36 and stethoscope receiving stem 30 whereby simultaneous use of all three connecting means can be effected. The plug 50 is adapted for use with ECG monitoring equipment by being connected to the amplifier inputs thereof. It is also to be understood that plug 50 can be eliminated and that the tube can be connected directly to appropriate monitoring devices.

From the foregoing, it will be appreciated that a highly unique and versatile multi-purpose probe has been devised. This probe, constituting a single tube in the manner of a heart and lung sound monitoring esophageal probe, includes a thin wall segment serving the dual purpose of coupling temperature variations and acoustic heart signals to the interior of the tube. Contained inside the tube, immediately next to the thin wall segment and isolated from gastric juices, is a uniquely oriented temperature sensing apparatus. The tube also includes a pair of active exposed electrodes which enable an adequate ECG signal to be derived without a ground electrode on the patient.

It is to be understood that numerous modifications may be made within the scope of the invention herein claimed. For example, it is contemplated that the esophageal probe may be made of such size as to permit intranasal introduction. Further, it is not necessary that the probe contain each of the temperature sensing, sound monitoring and electrode means. If desired, the probe may comprise temperature sensing and sound monitoring means alone or sound monitoring means with the necessary electrodes for electrocardiogram facilities.

The foregoing is illustrative of the principles of the invention. However, since modifications and changes may be apparent to one skilled in the art, it is not desired to limit the invention to the exact construction shown and described with it being considered that all suitable modifications and equivalents are in fact within the scope of the invention.

What is claimed is:

1. An endo-esophageal probe for monitoring acoustic heart and/or lung sounds and internal body temperatures comprising a tube having an upper segment and a lower end, said lower end adapted to be inserted into a lower portion of the esophagus through a body cavity, the portion of the tube adapted to be inserted into the body being sealed and including a thin wall segment and a thick wall, relatively rigid segment, at least a portion of said thin wall segment forming a diaphragm having a relatively low acoustic impedance relative to the thick wall segment for coupling the acoustic sounds to the interior of the tube, and temperature transducer means for monitoring the body temperature through the thin wall segment, electrical conductor means connected to said transducer means and extending to said upper segment, said transducer means being located inside the sealed tube in close proximity to the thin wall segment, said thin wall segment which is in close proximity to the transducer means being located on said lower end of the tube where the tube is normally situated in the lower mediastinum, below the pulmonary veins and between the heart and the descending part of the aorta, said thin wall segment located in close proximity to the temperature transducer means having a fast temperature response time relative to the thick wall segment for rapidly coupling internal body temperature variations to the transducer means.

2. The probe of claim 1 wherein at least a portion of the thin wall segment is located at a tip of the lower end, said temperature transducer means being located in close proximity to the tip.

3. The probe of claim 1 wherein said thin wall segment includes a plurality of spaced portions along the length of the lower end of the tube.

4. The probe of claim 1 wherein the tube includes a plurality of spaced apertures at the lower end thereof and an aperture at the tip, a thin sleeve bonded to the exterior of the tube and covering said apertures, said sleeve and apertures forming the thin wall segment, said sleeve and tube forming the thick wall segment.

5. An endo-esophageal probe for monitoring acoustic heart and/or lung sounds, electrocardiogram signals, and internal body temperatures comprising a tube having an upper segment and a lower end, said lower end adapted to be inserted into a lower portion of the esophagus through a body cavity, the portion of the tube adapted to be inserted into the body being sealed and including a thin wall segment and a thick wall, relatively rigid segment, at least a portion of said thin wall segment forming a diaphragm having a relatively low acoustic impedance relative to the thick wall segment for coupling the acoustic sounds to the interior of the tube, temperature transducer means for monitoring the body temperature through the thin wall segment, electrical conductor means connected to said transducer means and extending to said upper segment, said transducer means being located inside the sealed tube in close proximity to the thin wall segment, said thin wall segment which is in close proximity to the transducer means being located on said lower end of the tube where the tube is normally situated in the lower mediastinum, below the pulmonary veins and between the heart and the descending part of the aorta, said thin wall segment located in close proximity to the temperature transducer means having a fast temperature response time relative to the thick wall segment for rapidly coupling internal body temperature variations to the transducer means, a pair of spaced electrodes mounted on the exterior of the thick wall segment for monitoring the electrocardiogram signal, and electrical conductor means connected to said electrodes and extending to said upper segment.

6. The probe of claim 5 wherein at least a portion of the thin wall segment is located at a tip of the lower end, said temperature transducer means being located in close proximity to the tip.

7. The probe of claim 5 wherein said thin wall segment includes a plurality of spaced portions along the length of the lower end of the tube.

8. The probe of claim 5 wherein only a pair of spaced electrodes are provided on the tube and form active electrodes for ECG monitoring equipment.

9. The probe of claim 5 wherein the tube includes a plurality of spaced apertures at the lower end thereof and an aperture at the tip, a thin sleeve bonded to the exterior of the tube and covering said apertures, said sleeve and apertures forming the thin wall segment, said sleeve and tube forming the thick wall segment.

* * * * *